(12) United States Patent
Andrews et al.

(10) Patent No.: US 7,241,579 B2
(45) Date of Patent: Jul. 10, 2007

(54) METHOD OF SCREENING FOR GPR40 LIGANDS

(75) Inventors: John Leon Andrews, Durham, NC (US); Celia Patricia Briscoe, Durham, NC (US); Diane Michele Ignar, Durham, NC (US); Allison Isobel Muir, Brentford (GB); Howard Ray Sauls, Jr., Durham, NC (US); Mohammad Tadayyon, Hertford (GB)

(73) Assignees: SmithKline Beecham Corporation, Philadelphia, PA (US); SmithKline Beecham P.L.C., Brentford, Middlesex (GB)

( * ) Notice: Subject to any disclaimer, the term of this patent is extended or adjusted under 35 U.S.C. 154(b) by 553 days.

(21) Appl. No.: 10/451,007

(22) PCT Filed: Dec. 18, 2001

(86) PCT No.: PCT/US01/48985

§ 371 (c)(1),
(2), (4) Date: Jun. 18, 2003

(87) PCT Pub. No.: WO02/057783

PCT Pub. Date: Jul. 25, 2002

(65) Prior Publication Data

US 2004/0137517 A1    Jul. 15, 2004

(30) Foreign Application Priority Data

Dec. 22, 2000    (GB) ................................ 0031527.5

(51) Int. Cl.
*G01N 33/53* (2006.01)
*G01N 33/58* (2006.01)
*G01N 33/566* (2006.01)

(52) U.S. Cl. ........................................ 435/7.1; 435/7.2

(58) Field of Classification Search ...................... None
See application file for complete search history.

(56) References Cited

FOREIGN PATENT DOCUMENTS

| EP | 0849361 | 6/1998 |
|---|---|---|
| WO | WO 0022129 | 4/2000 |
| WO | WO 0244362 | 6/2002 |

OTHER PUBLICATIONS

Briscoe et al., The orphan G protein-coupled receptor GPR40 is activated by medium and long chain fatty acids. J. Biol. Chem. 278:11303-11311, 2003.*
Itoh et al., Free fatty acids regulate insulin secretion from pancreatic beta cells through GPR40. Nature 422:173-176, 2003.*
Sawzdargo et al., "A cluster of four novel human G protein-coupled receptor genes occurring in close proximity to CD22 gene on chromosome 19Q13.1," *Biochemical and Biophysical Research Communications* 239:543-547 (1997).
Sharif et al., "A high-throughput system for the evaluation of protein kinase C inhibitors based on ELK1 transcriptional activation in human astrocytoma cells," *International Journal of Oncology, Editorial Academy of the International Journal of Oncology* 14(2):326-335 (Feb. 1999).
Stables et al., "Development of a dual glow-signal firefly and renilla luciferase assay reagent for the analysis of G-protein coupled receptor signalling," *Journal of Receptor and Signal Transduction Research* 19(1-4):395-410 (1999).
Database EMBL 'Online!, Mar. 20, 2000, Database accession No. AW583167 abstract.
Database WPI, Section Ch, Week 200249, Derwent Publications, AN 2002-463740 & WO0244362 abstract.
Tseng et al., "Role of regulator of G protein signaling in desensitization of the glucose-dependent insulinotropic peptide receptor," *Endocrinology* 139(11):4470-4475 (Nov. 1998).
Warnotte et al., "Unbound rather than total concentration and saturation rather than unsaturation determine the potency of fatty acids on insulin secretion," *Molecular and Cellular Endocrinology* 153(1-2):147-153 (Jul. 1999).

* cited by examiner

*Primary Examiner*—Ruixiang Li
(74) *Attorney, Agent, or Firm*—Eric J. Kron

(57) ABSTRACT

Methods of screening for ligands of the GPR40 receptor are provided, including methods utilizing fatty acid GPR40 ligands.

3 Claims, 6 Drawing Sheets

SEQUENCE LISTING

```
<160> NUMBER OF SEQ ID NOS: 10

<210> SEQ ID NO 1
<211> LENGTH: 903
<212> TYPE: DNA
<213> ORGANISM: Homo sapiens
<220> FEATURE:
<221> NAME/KEY: CDS
<222> LOCATION: (1)..(900)

<400> SEQUENCE: 1 atg gac ctg ccc ccg cag ctc tcc ttc ggc ctc tat gtg gcc gcc ttt      48
Met Asp Leu Pro Pro Gln Leu Ser Phe Gly Leu Tyr Val Ala Ala Phe
1               5                   10                  15 gcg ctg ggc ttc ccg ctc aac gtc ctg gcc atc cga ggc gcg acg gcc      96
Ala Leu Gly Phe Pro Leu Asn Val Leu Ala Ile Arg Gly Ala Thr Ala
            20                  25                  30 cac gcc cgg ctc cgt ctc acc cct agc ctg gtc tac gcc ctg aac ctg     144
His Ala Arg Leu Arg Leu Thr Pro Ser Leu Val Tyr Ala Leu Asn Leu
        35                  40                  45 ggc tgc tcc gac ctg ctg ctg aca gtc tct ctg ccc ctg aag gcg gtg     192
Gly Cys Ser Asp Leu Leu Leu Thr Val Ser Leu Pro Leu Lys Ala Val
    50                  55                  60 gag gcg cta gcc tcc ggg gcc tgg cct ctg ccg gcc tcg ctg tgc ccc     240
Glu Ala Leu Ala Ser Gly Ala Trp Pro Leu Pro Ala Ser Leu Cys Pro
65                  70                  75                  80 gtc ttc gcg gtg gcc cac ttc ttc cca ctc tat gcc ggc ggg ggc ttc     288
Val Phe Ala Val Ala His Phe Phe Pro Leu Tyr Ala Gly Gly Gly Phe
                85                  90                  95 ctg gcc gcc ctg agt gca ggc cgc tac ctg gga gca gcc ttc ccc ttg     336
Leu Ala Ala Leu Ser Ala Gly Arg Tyr Leu Gly Ala Ala Phe Pro Leu
            100                 105                 110 ggc tac caa gcc ttc cgg agg ccg tgc tat tcc tgg ggg gtg tgc gcg     384
Gly Tyr Gln Ala Phe Arg Arg Pro Cys Tyr Ser Trp Gly Val Cys Ala
        115                 120                 125 gcc atc tgg gcc ctc gtc ctg tgt cac ctg ggt ctg gtc ttt ggg ttg     432
Ala Ile Trp Ala Leu Val Leu Cys His Leu Gly Leu Val Phe Gly Leu
    130                 135                 140 gag gct cca gga ggc tgg ctg gac cac agc aac acc tcc ctg ggc atc     480
Glu Ala Pro Gly Gly Trp Leu Asp His Ser Asn Thr Ser Leu Gly Ile
145                 150                 155                 160 aac aca ccg gtc aac ggc tct ccg gtc tgc ctg gag gcc tgg gac ccg     528
Asn Thr Pro Val Asn Gly Ser Pro Val Cys Leu Glu Ala Trp Asp Pro
                165                 170                 175 gcc tct gcc ggc ccg gcc cgc ttc agc ctc tct ctc ctc ttt ttt         576
Ala Ser Ala Gly Pro Ala Arg Phe Ser Leu Ser Leu Leu Phe Phe
            180                 185                 190 ctg ccc ttg gcc atc aca gcc ttc tgc tac gtg ggc tgc ctc cgg gca     624
Leu Pro Leu Ala Ile Thr Ala Phe Cys Tyr Val Gly Cys Leu Arg Ala
        195                 200                 205
```

```
ctg gcc cgc tcc ggc ctg acg cac agg cgg aag ctg cgg gcc gcc tgg      672
Leu Ala Arg Ser Gly Leu Thr His Arg Arg Lys Leu Arg Ala Ala Trp
    210                 215                 220 gtg gcc ggc ggg gcc ctc ctc acg ctg ctg ctc tgc gta gga ccc tac      720
Val Ala Gly Gly Ala Leu Leu Thr Leu Leu Leu Cys Val Gly Pro Tyr
225                 230                 235                 240 aac gcc tcc aac gtg gcc agc ttc ctg tac ccc aat cta gga ggc tcc      768
Asn Ala Ser Asn Val Ala Ser Phe Leu Tyr Pro Asn Leu Gly Gly Ser
                245                 250                 255 tgg cgg aag ctg ggc ctc atc acg ggt gcc tgg agt gtg gtg ctt aat      816
Trp Arg Lys Leu Gly Leu Ile Thr Gly Ala Trp Ser Val Val Leu Asn
            260                 265                 270 ccg ctg gtg acc ggt tac ttg gga agg ggt cct ggc ctg aag aca gtg      864
Pro Leu Val Thr Gly Tyr Leu Gly Arg Gly Pro Gly Leu Lys Thr Val
        275                 280                 285 tgt gcg gca aga acg caa ggg ggc aag tcc cag aag taa                  903
Cys Ala Ala Arg Thr Gln Gly Gly Lys Ser Gln Lys
    290                 295                 300

<210> SEQ ID NO 2
<211> LENGTH: 300
<212> TYPE: PRT
<213> ORGANISM: Homo sapiens

<400> SEQUENCE: 2

Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
                20                  25                  30

His Ala Arg Leu Arg Leu Thr Pro Ser Leu Val Tyr Ala Leu Asn Leu
            35                  40                  45

Gly Cys Ser Asp Leu Leu Leu Thr Val Ser Leu Pro Leu Lys Ala Val
        50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Ala Phe Pro Leu
                100                 105                 110

Gly Tyr Gln Ala Phe Arg Arg Pro Cys Tyr Ser Trp Gly Val Cys Ala
            115                 120                 125

Ala Ile Trp Ala Leu Val Leu Cys His Leu Gly Leu Val Phe Gly Leu
        130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Ala Trp
    210                 215                 220

Val Ala Gly Gly Ala Leu Leu Thr Leu Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255
```

```
Trp Arg Lys Leu Gly Leu Ile Thr Gly Ala Trp Ser Val Val Leu Asn
            260                 265                 270

Pro Leu Val Thr Gly Tyr Leu Arg Gly Pro Gly Leu Lys Thr Val
        275                 280                 285

Cys Ala Ala Arg Thr Gln Gly Gly Lys Ser Gln Lys
    290                 295                 300

<210> SEQ ID NO 3
<211> LENGTH: 903
<212> TYPE: DNA
<213> ORGANISM: Mus musculus
<220> FEATURE:
<221> NAME/KEY: CDS
<222> LOCATION: (1)..(900)

<400> SEQUENCE: 3 atg gac ctg ccc cca cag ctc tcc ttc gct ctc tat gta tct gcc ttt     48
Met Asp Leu Pro Pro Gln Leu Ser Phe Ala Leu Tyr Val Ser Ala Phe
1               5                   10                  15 gcg ctg ggc ttt cca ttg aac ttg tta gcc atc cga ggc gca gtg tcc     96
Ala Leu Gly Phe Pro Leu Asn Leu Leu Ala Ile Arg Gly Ala Val Ser
            20                  25                  30 cac gct aaa ctg cga ctc act ccc agc ttg gtc tac act ctc cat ctg    144
His Ala Lys Leu Arg Leu Thr Pro Ser Leu Val Tyr Thr Leu His Leu
        35                  40                  45 ggc tgc tct gat ctc cta ctg gcc atc act ctg ccc ctg aag gct gtg    192
Gly Cys Ser Asp Leu Leu Leu Ala Ile Thr Leu Pro Leu Lys Ala Val
    50                  55                  60 gag gcc ctg gct tct gga gcc tgg ccc ctg ccg ctc ccc ttc tgc cca    240
Glu Ala Leu Ala Ser Gly Ala Trp Pro Leu Pro Leu Pro Phe Cys Pro
65                  70                  75                  80 gtc ttt gcc ttg gcc cac ttt gct ccc ctc tac gca ggc gga ggc ttc    288
Val Phe Ala Leu Ala His Phe Ala Pro Leu Tyr Ala Gly Gly Gly Phe
                85                  90                  95 cta gct gct ctc agc gct ggc cgc tac ctg ggg gct gcc ttc ccc ttc    336
Leu Ala Ala Leu Ser Ala Gly Arg Tyr Leu Gly Ala Ala Phe Pro Phe
            100                 105                 110 ggg tac caa gcc atc cgg agg ccc cgc tat tcc tgg ggt gtg tgt gtg    384
Gly Tyr Gln Ala Ile Arg Arg Pro Arg Tyr Ser Trp Gly Val Cys Val
        115                 120                 125 gct ata tgg gcc ctt gtc ctc tgc cac ctg ggg ctg gcc ctt ggc ttg    432
Ala Ile Trp Ala Leu Val Leu Cys His Leu Gly Leu Ala Leu Gly Leu
    130                 135                 140 gag act tcc gga agc tgg ctg gac aac agt acc agt tcc ctg ggc atc    480
Glu Thr Ser Gly Ser Trp Leu Asp Asn Ser Thr Ser Ser Leu Gly Ile
145                 150                 155                 160 aac ata ccc gtg aat ggc tcc ccg gtc tgc ctg gaa gcc tgg gat ccc    528
Asn Ile Pro Val Asn Gly Ser Pro Val Cys Leu Glu Ala Trp Asp Pro
                165                 170                 175 gac tct gcc cgc cct gcc cgt ctc agt ttc tcc att ctg ctc ttc ttt    576
Asp Ser Ala Arg Pro Ala Arg Leu Ser Phe Ser Ile Leu Leu Phe Phe
            180                 185                 190 ctg ccc ttg gtc atc act gcc ttc tgc tat gtg ggc tgc ctc cgg gcc    624
Leu Pro Leu Val Ile Thr Ala Phe Cys Tyr Val Gly Cys Leu Arg Ala
        195                 200                 205 ctg gtg cgc tca ggc ctg agc cac aaa cgg aag ctc agg gca gct tgg    672
Leu Val Arg Ser Gly Leu Ser His Lys Arg Lys Leu Arg Ala Ala Trp
    210                 215                 220 gtg gcc gga ggc gct ctc ctc aca ctc ctg ctc tgc ctg ggg ccc tat    720
Val Ala Gly Gly Ala Leu Leu Thr Leu Leu Leu Cys Leu Gly Pro Tyr
```

```
aat gcc tcc aat gtg gct agt ttc ata aac ccg gac cta gga ggc tcc    768
Asn Ala Ser Asn Val Ala Ser Phe Ile Asn Pro Asp Leu Gly Gly Ser
            245                 250                 255 tgg agg aag ttg gga ctc atc aca ggg gcc tgg agt gtg gta ctc aac    816
Trp Arg Lys Leu Gly Leu Ile Thr Gly Ala Trp Ser Val Val Leu Asn
            260                 265                 270 cca ctg gtc act ggc tac ttg gga aca ggt cct gga cgg gga aca ata    864
Pro Leu Val Thr Gly Tyr Leu Gly Thr Gly Pro Gly Arg Gly Thr Ile
            275                 280                 285 tgt gtg acg agg act caa aga gga aca att cag aag tag                903
Cys Val Thr Arg Thr Gln Arg Gly Thr Ile Gln Lys
            290                 295                 300

<210> SEQ ID NO 4
<211> LENGTH: 300
<212> TYPE: PRT
<213> ORGANISM: Mus musculus

<400> SEQUENCE: 4

Met Asp Leu Pro Pro Gln Leu Ser Phe Ala Leu Tyr Val Ser Ala Phe
 1               5                  10                  15

Ala Leu Gly Phe Pro Leu Asn Leu Leu Ala Ile Arg Gly Ala Val Ser
                20                  25                  30

His Ala Lys Leu Arg Leu Thr Pro Ser Leu Val Tyr Thr Leu His Leu
            35                  40                  45

Gly Cys Ser Asp Leu Leu Leu Ala Ile Thr Leu Pro Leu Lys Ala Val
    50                  55                  60

Glu Ala Leu Ala Ser Gly Ala Trp Pro Leu Pro Leu Pro Phe Cys Pro
65                  70                  75                  80

Val Phe Ala Leu Ala His Phe Ala Pro Leu Tyr Ala Gly Gly Gly Phe
                85                  90                  95

Leu Ala Ala Leu Ser Ala Gly Arg Tyr Leu Gly Ala Ala Phe Pro Phe
                100                 105                 110

Gly Tyr Gln Ala Ile Arg Arg Pro Arg Tyr Ser Trp Gly Val Cys Val
            115                 120                 125

Ala Ile Trp Ala Leu Val Leu Cys His Leu Gly Leu Ala Leu Gly Leu
130                 135                 140

Glu Thr Ser Gly Ser Trp Leu Asp Asn Ser Thr Ser Ser Leu Gly Ile
145                 150                 155                 160

Asn Ile Pro Val Asn Gly Ser Pro Val Cys Leu Glu Ala Trp Asp Pro
                165                 170                 175

Asp Ser Ala Arg Pro Ala Arg Leu Ser Phe Ser Ile Leu Leu Phe Phe
            180                 185                 190

Leu Pro Leu Val Ile Thr Ala Phe Cys Tyr Val Gly Cys Leu Arg Ala
            195                 200                 205

Leu Val Arg Ser Gly Leu Ser His Lys Arg Lys Leu Arg Ala Ala Trp
        210                 215                 220

Val Ala Gly Gly Ala Leu Leu Thr Leu Leu Cys Leu Gly Pro Tyr
225                 230                 235                 240

Asn Ala Ser Asn Val Ala Ser Phe Ile Asn Pro Asp Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Thr Gly Pro Gly Arg Gly Thr Ile
            275                 280                 285
```

```
Cys Val Thr Arg Thr Gln Arg Gly Thr Ile Gln Lys
    290                 295                 300
```

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: Forward primer for human GPR40

<400> SEQUENCE: 5
gtggtgctta atccgctggt                                              20

<210> SEQ ID NO 6
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Reverse primer for human GPR40

<400> SEQUENCE: 6
tggcgttact tctgggactt g                                            21

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: ()..()
<223> OTHER INFORMATION: Probe for human GPR40

<400> SEQUENCE: 7
cttgcgttct tgccgcacac actgt                                        25

<210> SEQ ID NO 8
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: Forward primer for mouse/rat GPR40

<400> SEQUENCE: 8
agttccctgg gcatcaacat a                                            21

<210> SEQ ID NO 9
<211> LENGTH: 22
<212> TYPE: DNA
<213> ORGANISM: Artificial Sequence
<220> FEATURE:
<221> NAME/KEY: misc_feature
<222> LOCATION: ()..()
<223> OTHER INFORMATION: Reverse primer for mouse/rat GPR40

<400> SEQUENCE: 9
caagggcaga aagaagagca ga                                           22

<210> SEQ ID NO 10
<211> LENGTH: 22
<212> TYPE: DNA
<213> ORGANISM: Artificial Sequence

```
-continued

<220> FEATURE:
<221> NAME/KEY: misc_feature
<222> LOCATION: ()..()
<223> OTHER INFORMATION: Probe for mouse/rat GPR40

<400> SEQUENCE: 10
aatggctccc cggtctgcct gg                                              22
```

METHOD OF SCREENING FOR GPR40 LIGANDS

This application is filed pursuant to 35 U.S.C. § 371 as a United States National Phase Application of International Application No. PCT/US01/48985 filed Dec. 18, 2001, which claims priority from Great Britain Application No. 0031527.5 filed Dec. 22, 2000.

TECHNICAL FIELD

This invention relates to the identification of a ligand for a G-protein coupled receptor (GPCR) and its use in screening methods, and rational drug design, to identify antagonists and agonists of the receptor, to the antagonists and agonists so identified and their use in therapy.

BACKGROUND

The membrane protein gene superfamily of G-protein coupled receptors (GPCRs) has been characterized as having seven putative transmembrane domains. The domains are believed to represent transmembrane α-helices connected by extracellular and cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptor transmembrane domains, which socket is surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters. See Johnson, et al., Endoc. Rev., (1989) 10: 317–331). Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found at numerous sites within a mammalian host.

Over the past 15 years, nearly 150 therapeutic agents targeting 7 transmembrane (7 TM) receptors have been successfully introduced onto the market, thereby establishing their value as therapeutic targets.

SUMMARY

A first aspect of the present invention is a method of screening a test compound to determine whether the compound is a GPR40 receptor ligand. The method comprises detecting whether the test compound competitively inhibits the binding of a fatty acid GPR40 ligand to a GPR40 receptor.

A further aspect of the present invention is a method of screening a compound for GPR40 antagonist activity. The method comprises providing a test cell expressing on its surface a GPR40 receptor, and containing a reporter construct comprising a Gq responsive transcriptional element and a reporter gene, where expression of the reporter gene produces a detectable signal. The test cell surface is exposed to a GPR40 fatty acid agonist under conditions that permit binding of a GPR40 fatty acid agonist, and then exposed to a test compound. Any detectable signal produced by the reporter gene is measured, and compared to the detectable signal that would be expected to be produced if the cell were exposed only to the GPR40 agonist. A decrease in the detectable signal indicates the test compound is a GPR40 antagonist.

A further aspect of the present invention is a method of screening a compound for GPR40 agonist activity. The method comprises providing a cell expressing on its surface a GPR40 receptor, and containing a reporter construct comprising a responsive transcriptional element and a reporter gene, where expression of the reporter gene produces a detectable signal. The responsive transcriptional element may be a Gi responsive transcriptional element, a Gq responsive transcriptional element, or a Gi/Gq responsive transcriptional element. The test compound is contacted to the cell surface under conditions that permit binding of a GPR40 ligand to the GPR40 receptor, and reporter gene expression is detected.

A further aspect of the present invention is a method of screening a compound for GPR40 antagonist activity. The method comprises providing a cell expressing on its surface a GPR40 receptor, and containing a reporter construct comprising a responsive transcriptional element and a reporter gene, where expression of the reporter gene produces a detectable signal. The responsive transcriptional element may be a Gi responsive transcriptional element, a Gq responsive transcriptional element, or a Gi/Gq responsive transcriptional element. The cell surface is exposed to a test compound and a GPR40 agonist under conditions that permit binding of a GPR40 ligand to the GPR40 receptor, and reporter gene expression is detected. Decreased reporter gene expression in the presence of both test compound and agonist, compared to reporter gene expression in the presence of the GPR40 agonist only, indicates that the test compound is a GPR40 antagonist.

A further aspect of the present invention is a method of screening a compound for GPR40 antagonist activity where the method comprises detecting whether a test compound decreases glucose-stimulated insulin release from, or production by, mammalian pancreatic beta cells in the presence of a GPR40 agonist, compared to glucose-stimulated insulin release that would occur due to the presence of the GPR40 agonist.

A further aspect of the present invention is a method of screening a compound for GPR40 agonist activity, comprising detecting whether the compound binds to GPR40 and increases glucose-stimulated insulin release from, or production by, mammalian pancreatic beta cells.

DETAILED DESCRIPTION

Figure 1:
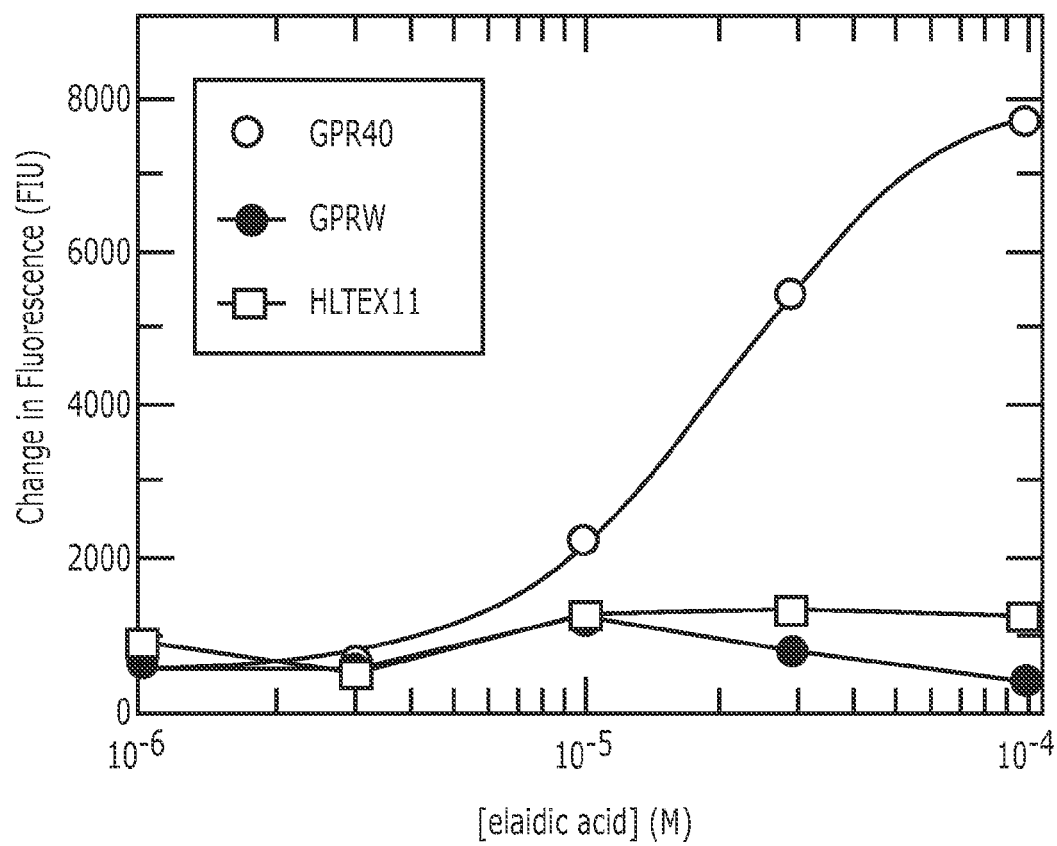
FIG. 1 shows the calcium response (measured by change in fluorescence) of GPR40 to the fatty acid elaidic acid in HEK-293 cells transiently expressing either GPR40, the 7TM receptor GPRW, or the 7TM receptor HLTEX11.

GPR40 is a recently described orphan G-protein coupled receptor isolated during a search for novel receptors (Sawzdargo, M. (1997) Biochem. Biophys. Res. Commun. 239 (2), 543–547). The polynucleotide sequence of human GPR40 (GenBank Accession no. NM_005303) is given in SEQ ID NO:1 herein, and the amino acid sequence of the polypeptide encoded thereby is given in SEQ ID NO:2 herein.

More recently a mouse GPR40 orthologue has been cloned and sequenced (U.S. patent application No. 60/234, 253, SmithKline Beecham). The polynucleotide sequence of mouse GPR40 is given in SEQ ID NO:3 herein and the polypeptide encoded thereby has the amino acid sequence of SEQ ID NO:4 herein.

The present invention is based on the unusual and unexpected finding that the human GPR40 receptor is specifically activated by both saturated and unsaturated fatty acids. Further, it has been shown that GPR40 is expressed in the human pancreas, more specifically the β cells of the pancreatic islets.

The present inventors determined that the GPR40 receptor can constitutively act through a pertussis toxin sensitive G protein. Both Gi and Go (and subtypes thereof) proteins are known to be pertussis toxin sensitive. However, the present inventors carried out further research to determine that fatty acids were GPR40 ligands that acted via Gq protein (pertussis toxin insensitive G protein).

Many studies have shown that acute treatment of islets with fatty acids (1–3 hrs) stimulates glucose-stimulated insulin secretion, whereas longer periods of treatment (6–24 hrs) are inhibitory to glucose-stimulated insulin secretion (Warnotte C. et al (1994). Diabetes 43(5):703–711; Zhou Y P. et al (1996) Metabolism: Clinical & Experimental. 45(8): 981–986). There is mounting evidence that shows that an increase in plasma fatty acid levels may be detrimental to β-cell function (lipotoxicity). Studies in the ZDF rats, frequently used as a model of diabetes, have shown that increased levels of circulating fatty acids leads to the production of ceramide, activation of nitric oxide synthase, and apoptosis of β-cells (Shimabukuro M., et al (1998) Proc. Natl. Acad. Sci. U.S.A. 95: 2498–2502). We have found that expression of GPR40 is enriched in human pancreatic islets by 2–100 fold (four individual samples analysed) for an equivalent RNA input compared to human total pancreatic RNA. This tissue localisation suggests that the receptor may have a role in β-cell function. The finding that fatty acids are ligands for GPR40 may aid in the elucidation of GPR40 function in the β-cell. A consequence of acute receptor activation may therefore be enhancement of glucose-stimulated insulin secretion whereas longer periods may be expected to lead to decreases in glucose-stimulated insulin secretion and genes associated with glucose-sensitivity of β-cells e.g. glucokinase. On this basis, it is possible that either agonists or antagonists to GPR40 may be of therapeutic value for diabetes, and particularly type 2 diabetes.

Treatment with a GPR40 agonist may be expected therefore to increase glucose-stimulated insulin secretion from β-cells in the short term. GPR40 antagonists may be of therapeutic value with respect to possible reductions in lipotoxicity and thus function to improve β-cell function.

This identification of fatty acids as ligands for GPR40 therefore facilitates the development of screening methods for identifying agonists and antagonists of the receptor.

Accordingly, the present invention provides a method of identifying compounds which bind to and activate (agonist) or inhibit activation (antagonist) of the GPR40 receptor which method comprises using GPR40, in combination with fatty acid GPR40 ligands of C6–C23 saturated or unsaturated fatty acid, optionally containing up to 6 alkene or 3 acetylene bonds, optionally cyclic or branched, and optionally substituted with 1–3 hydroxy groups.

As used herein, "GPR40" refers to a receptor polypeptide having at least 95% identity to the polypeptide sequence given in SEQ ID NO:2, and having GPR40 function; GPR40 receptor polypeptides used in the methods of the present invention are preferably mammalian, and more preferably human. GPR40 also refers to derivatives of the receptor useful in the screening or rational drug design methods disclosed herein. Such derivatives include portions of the polypeptide of SEQ ID NO:2 which retain ligand binding function.

Preferably the fatty acid ligand is selected from the group consisting of:
1) trans-retinoic acid (Vitamin A acid; Tretinoin) $C_{20}H_{28}O_2$ (Unsat)
2) cis-4,7,10,13,16,19-Docosahexaenoic acid $C_{22}H_{32}O_2$ (Unsat)
3) Palmitic acid $C_{16}H_{32}O_2$ (Sat)
4) Pentadeconoic acid $C_{15}H_{30}O_2$ (Sat)
5) Elaidic acid $C_{18}H_{34}O_2$ (Unsat)
6) Petroselinic acid $C_{18}H_{34}O_2$ (Unsat)
7) Heptadecanoic acid $C_{17}H_{34}O_2$ (Sat)
8) Tridecanoic acid $C_{13}H_{26}O_2$ (Sat)
9) Lauric acid (Dodecanoic acid) $C_{12}H_{24}O_2$ (Sat)
10) Arachidonic acid $C_{20}H_{32}O_2$ (Unsat)
11) Linolenic acid $C_{18}H_{30}O_2$ (Unsat)
12) Palmitoleic acid $C_{16}H_{30}O_2$ (Unsat)
13) Capric acid $C_{10}H_{20}O_2$ (Sat)
14) Myristic acid $C_{14}H_{28}O_2$ (Sat)
15) Stearic acid $C_{18}H_{36}O_2$ (Sat)
16) Undecanoic acid $C_{11}H_{22}O_2$ (Sat)
16) Eicosatriynoic acid In this list "sat" refers to saturated and "unsat" refers to unsaturated fatty acid.

As used hereinbelow the term "fatty acid ligand" is defined as a fatty acid ligand of the invention, which ligand is a C6–C23 saturated or unsaturated fatty acid, optionally containing up to 6 alkene or 3 acetylene bonds, optionally cyclic or branched, and optionally substituted with 1–3 hydroxy groups.

Compounds identified using the methods of the invention may be useful in the treatment of type II diabetes (non-insulin dependent diabetes mellitus, NIDDM) and obesity, glucose intolerance, insulin resistance, neurodegenerative disease (for example Alzheimer's disease) and other indications such as stroke.

In a first embodiment, an agonist or antagonist of GPR40 may be identified by contacting a cell expressing on the surface thereof the receptor GPR40, said receptor being associated with a second component capable of providing a detectable signal in response to the binding of a compound to said receptor, with a compound to be screened under conditions to permit binding to the receptor; and determining whether the compound binds to, and activates, or inhibits, the receptor, by detecting the presence or absence of a signal generated from the interaction of the compound with the receptor, optionally in the presence of labeled or unlabeled ligand, for example a fatty acid ligand.

In a further embodiment, an agonist or antagonist of GPR40 may be identified by determining the inhibition of binding of a ligand (e.g., a fatty acid ligand) to cells which have the GPR40 receptor on the surface thereof, or to cell membranes containing the receptor, in the presence of a candidate compound and under conditions permitting binding to the receptor. By determining the amount of ligand bound to the receptor, a compound capable of causing reduction of binding of a ligand is identified as an agonist or antagonist of GPR40.

In general, such screening methods involve providing appropriate cells which express GPR40 on the surface thereof. Such cells include cells from mammals (e.g., Chinese hamster ovary (CHO), HEK (human embryonic kidney), Beta cells of pancreatic islets), melanophore cells, and cells of *Drosophila* or *E. coli*. In particular, a polynucleotide encoding GPR40 is employed to transfect cells to thereby express said receptor. Construction of expression vectors comprising a GPR40-encoding polynucleotide and transfection of cells with said GPR40 expression vectors can be achieved using standard methods, as described in, for example, Sambrook et al., Molecular Cloning: A Laboratory Manual, $2^{nd}$ Ed., Cold Spring Harbor Laboratory Press, Cold Spring Harbor, N.Y. (1989). Receptor expression may be transient or stable. Preferably, the expression is stable. More preferably a mammalian cell line is transfected with an expression vector comprising a nucleic acid sequence encoding the GPR40 receptor, for example the polynucleotide of SEQ ID NO:1, or the coding region thereof, and the cell line then cultured in a culture medium such that the receptor is stably expressed on the surface of the cell. The expressed receptor is then contacted with a test compound to observe binding, stimulation or inhibition of a functional response, in the presence or absence of a ligand (such as a fatty acid ligand as hereinabove described).

Assays as described herein may utilize intact cells expressing functional GPR40, or cell membranes containing the receptor, as is known in the art.

Alternatively a soluble portion of the GPR40 receptor (ie. not membrane-bound) comprising the ligand binding domain may be expressed in the soluble fraction, either in the intracellular compartment or secreted out of the cell into the medium. Techniques for the isolation and purification of expressed soluble receptors are well known in the art.

An example of a screening method includes expressing GPR40 in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are ligands of GPR40 by determining the inhibition of binding of a labeled ligand (such as a fatty acid ligand) to cells which have the receptor on the surface thereof, or to cell membranes containing the receptor. Such a method involves transfecting a eukaryotic cell with DNA encoding GPR40 such that the cell expresses the receptor on its surface. The cell is then contacted with a test compound in the presence of a labeled form of a ligand, such as a labelled fatty acid ligand. The ligand can be labeled using any suitable method as is known in the art, including radioactivity (e.g., with $^{125}$Iodine), fluorescent compounds, β-glucuronidase, luciferase, etc. The amount of labeled ligand bound to the receptors is measured, e.g., by measuring radioactivity associated with transfected cells or membranes from these cells. If the test compound binds to the receptor, the binding of labeled ligand to the receptor is inhibited as determined by a reduction of labeled ligand which binds to the receptors. This method is generally referred to as a binding assay.

A further screening method involves the use of mammalian cells which are transfected to express functional GPR40. The cells are loaded with an indicator dye that produces a fluorescent signal when bound to calcium, and the cells are contacted with a test substance and/or a receptor agonist, such as a fatty acid ligand. Any change in fluorescent signal is measured over a defined period of time using, for example, a fluorescence spectrophotometer or a fluorescence imaging plate reader. A change in the fluorescence signal pattern generated by the ligand indicates that a compound is a potential agonist for the receptor. A decrease in the fluorescence signal pattern generated by the agonist in the presence of the test compound indicates that a compound is potential antagonist for the receptor.

Another method involves screening for GPR40 ligands by determining effects on receptor-mediated cAMP and/or adenylyl cyclase accumulation. Such a method involves transiently or stably transfecting a eukaryotic cell with GPR40 to express the receptor on the cell surface. The cell is then exposed to test compounds in the presence or absence of a GPR40 agonist, such as a fatty acid. The change in cAMP level is then measured over a defined period of time, for example, by radio-immuno or protein binding assays (for example using FlashPlates (PerkinElmer Life Sciences) or a scintillation proximity assay). Changes in cAMP levels can also be determined by directly measuring the activity of the enzyme, adenylate cyclase, in broken cell preparations. If the test compound binds the receptor and affects GPR40 activation, the levels of GPR40-mediated cAMP, or adenylate cyclase activity, will be reduced or increased.

Various methods are known in the art to detect GPCR activation, depending in part on the G-protein to which the receptor is coupled. For example, activation of the Gi pathway decreases adenylyl cyclase activity, and Gi signaling may be detected by measuring the inhibition of forskolin-stimulated cAMP accumulation. (Wong et al., Methods Enzymology, 238:81 (1994)).

The use of reporter-based assays is known in the art to identify GPCR ligands. In general, such assays utilize recombinant cells expressing a functional target receptor protein whose signal transduction activity is modulated by interaction with an extracellular ligand, with the transduction activity being able to generate a detectable signal. See, e.g., Chen et al., J. Pharmacol. Toxicol. 42:199 (1999); Stables et al., J. Recept. Signal Transduct. Res. 19:395 (1999).

To illustrate, the transduced intracellular signal is initiated by the specific interaction of an extracellular ligand with the receptor on the cell surface. This interaction initiates a series of intracellular events that result in a rapid and detectable change in the transcription or translation of a gene. By selecting transcriptional regulatory sequences that are responsive to the transduced intracellular signals and operatively linking the selected promoters to reporter genes whose transcription, translation or ultimate activity is readily detectable and measurable, the transcription based assay indicates whether a specific receptor interacts with a test compound to influence intracellular transduction. See, e.g., Himmler et al., J. Receptor Res. 13:79 (1993); Weyer et al., Receptors and Channels 1:193 (1993); Bevan et al., Neuroreport 9:2703 (1998).

Using such assays, test compounds that induce receptor signaling can be identified (agonists). Alternatively, the assay can test compounds for the ability to potentiate the induction response generated by treatment of the cell with a known agonist. If the test compound does not appear to directly induce the activity of the receptor protein, the assay may be repeated with the recombinant cell first being contacted with a known activator of the target receptor to induce the signal transduction pathway (and generate the detectable signal). Test compounds may then be assayed for the ability to antagonize (inhibit or block) the activation of the receptor by a known agonist activator.

As used herein, an "agonist" refers to agents which either induce activation of receptor signalling pathways, e.g., such as by mimicking a ligand for the receptor, as well as agents which potentiate the sensitivity of the receptor to a ligand, e.g., lower the concentrations of ligand required to induce a particular level of receptor-dependent signalling.

Cells utilized in such assays may express the receptor of interest endogenously, or may be engineered to express a heterologous target receptor protein. Methods for introducing heterologous DNA into eukaryotic cells are known in the art and any suitable method may be used. As is known in the art, it may be desirable to inactivate one or more endogenous genes of the host cells (e.g., the gene for the homologous receptor). Additionally, other proteins involved in signal transduction from the target receptor can be inactivated, or complemented with an ortholog or paralog from another organism, e.g., yeast G protein subunits can be complemented by mammalian G protein subunits in yeast cells also engineered to express a mammalian G protein coupled receptor.

The host cell may contain a reporter construct comprising a reporter gene in operative linkage with one or more transcriptional regulatory elements responsive to the signal transduction activity of the receptor protein. Exemplary reporter genes include enzymes (e.g., luciferase, phosphatase, secreted alkaline phosphatase, β-galactosidase, green fluorescent protein, beta lactamase, chloramphenicol acetyl transferase) which can produce a spectrometrically active label (e.g., changes in color, fluorescence or luminescence), or a gene product which alters a cellular phenotype (e.g., cell growth, drug resistance or auxotrophy).

As used herein, a "reporter gene construct" is a nucleic acid molecule that includes a reporter gene operatively linked to transcriptional regulatory sequence(s) or element(s) which control transcription of the reporter gene. The activity of at least one or more of these control sequences is directly or indirectly regulated by the target receptor protein. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences are recognized by effector molecules, including those that are specifically induced by interaction of an extracellular signal with the target receptor. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nucleotides that alter translation of the resulting mRNA, thereby altering the amount of reporter gene product.

The level of expression of the reporter gene provides the receptor-dependent detection signal. The amount of transcription from the reporter gene may be measured using any suitable method known to those of skill in the art. For example, specific mRNA expression may be detected using Northern blots or real-time quantitative Polymerase Chain Reaction (PCR) such as that available as TAQMAN®; or specific protein product may be identified by a characteristic stain or an intrinsic activity. The reporter gene may encode a gene product that, by enzymatic activity, gives rise to a detection signal based on color, fluorescence, or luminescence. The response of the reporter gene is then compared to the response in either the same cell in the absence of the test compound, or it may be compared with the response in a substantially identical cell that lacks the specific receptors. Any statistically or otherwise significant difference in the response indicates that the test compound has altered the activity of the specific receptor.

Agonists and antagonists are "receptor effector" molecules that modulate signal transduction via the receptor. Receptor effector molecules are capable of binding to the receptor, though not necessarily at the binding site of the natural ligand. Receptor effectors can modulate signal transduction when used alone (surrogate ligands), or can alter signal transduction in the presence of the natural ligand, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The terms "receptor activator" and "surrogate ligand" refer to an agonist which induces signal transduction from a receptor.

"Signal transduction" is the processing of chemical signals from the cellular environment through the cell membrane, and may occur through one or more of several mechanisms, such as phosphorylation, activation of ion channels, effector enzyme activation via guanine nucleotide binding protein intermediates, formation of inositol phosphate, activation of adenylyl cyclase, and/or direct activation (or inhibition) of a transcriptional factor. The term "modulation of a signal transduction activity of a receptor protein" in its various grammatical forms, as used herein, designates induction and/or potentiation, as well as inhibition of one or more signal transduction pathways downstream of a receptor.

Methods utilizing pigment cells for identifying GPCR ligands are known in the art. In general, the method utilizes pigment cells capable of dispersing or aggregating pigment in response to a receptor-mediated stimulus, and which express an exogenous G-protein coupled receptor. The condition of the pigment (aggregation or dispersion) in response to a test compound indicates whether the test compound interacts with the expressed GPCR. See, e.g., U.S. Pat. No. 5,462,856; U.S. Pat. No. 6,051,386.

*Xenopus laevis* melanophores are able to functionally express recombinant receptors which couple via G-proteins to adenylate cyclase or phospholipase C (PLC). Receptor-mediated stimulation of either of these enzymes causes dispersion of melanosomes, while receptor stimulation that inhibits adenylate cyclase induces melanosome aggregation. Various assays have been devised utilizing *Xenopus* melanophores transfected with a GPCR of interest, to detect the agonist (or antagonist) effects of test compounds on the receptors. See, e.g., Chen et al., J. Pharmacol. Toxicol. 42:199 (1999); McClintock et al., Anal. Biochem. 209:298 (1993); Potenza et al., Anal Biochem 206:315 (1992); Potenza et al., Pigment Cell Res 5:372 (1992)).

The Fluorometric Imaging Plate Reader (FLIPR™, Molecular Devices, UK) measures intracellular fluorescense in multi-well microplates. Where a GPCR couples to a calcium signalling pathway, the FLIPR system can be used with cells expressing the G-protein coupled receptor and containing calcium-sensitive fluorescent dyes, to monitor the intracellular calcium flux that occurs after activation of the G-coupled receptor. See, e.g., Kirk et al., J. Biomolecular Screening, 1:75 (1996).

Certain GPCRs do not couple with calcium signalling pathways, while others may not signal through calcium pathways depending on the type of cell in which the receptor is expressed. In such situations, chimeric G proteins have been utilized to link the receptor to calcium signalling in transfected cells, thereby allowing the use of high throughput FLIPR assays. (Wada et al., Developing a High Throughput Functional Screening Assay for Gi/o-coupled Cloned Receptors using the FLIPR™ System, published by Molecular Devices, 2001; Coward et al., Chimeric G-proteins allow a high-throughput signaling assay of Gi-coupled receptors, Analytical Biochemistry 270:242 (1999)). Coward et al report the use of chimeric G proteins that allow Gi-coupled receptors to signal through Gq and generate a detectable calcium response in CHO cells, measured using FLIPR™ technology.

Accordingly the present invention provides methods of screening test compounds to determine whether the compound is a GPR40 receptor ligand, by detecting whether the test compound competitively inhibits the binding of a fatty acid GPR40 ligand to a GPR40 receptor. The fatty acid ligand may be labeled with a detectable label as is well known in the art. As used herein, detectable labels include moieties that can be detected by visual inspection (e.g., that include or produce colored elements), or detected with the aid of artificial detection systems, including. e.g., optical systems, spectroscopic systems, radiographic systems, and the like. The detectable label may be selected from among radioisotopes, fluorescent dyes, and enzymes.

The present invention also provides methods of screening test compounds for GPR40 antagonist activity. One such method utilizes a test cell expressing on its surface a GPR40 receptor, and containing a reporter construct comprising a Gq responsive transcriptional element and a reporter gene, where expression of the reporter gene produces a detectable signal. The test cell surface is exposed to a GPR40 fatty acid agonist under conditions that permit binding of the GPR40 fatty acid agonist to the GPR40 receptor, and then the cell surface is exposed to the test compound under similar conditions. The detectable signal produced by the reporter gene is then measured, and compared to the detectable signal that would be expected to occur in the presence of the GPR40 fatty acid agonist only (i.e., in the absence of the test compound). This comparison may be a side-by-side comparison of the detectable signal in a control cell (i.e., a cell similar in all ways to the test cell, but exposed to the GPR40 fatty acid agonist in the absence of test compound). Alternatively the comparison may be to a standard that is determined prior to or after the test cell is processed, i.e., a control experiment that was conducted prior to or after the detectable signal to establish a quantitative or qualitative standard that is used in the comparison.

The present invention further provides methods of screening a compound for GPR40 agonist activity. One such method utilizes a cell expressing GPR40 receptors on its surface, and containing a reporter construct comprising a responsive transcriptional element and a reporter gene, where expression of the reporter gene produces a detectable signal. The transcriptional element may be a Gi responsive transcriptional element, a Gq responsive transcriptional element, or a Gi/Gq responsive transcriptional element. The cell surface is contacted with (i.e., exposed to) a test compound, under conditions that permit binding of a GPR40 ligand to the GPR40 receptor, and any reporter gene expression is detected (indicating that the test compound has GPR40 agonist activity).

The present invention further provides methods of screening a compound for GPR40 antagonist activity. One such method utilizes a cell expressing on its surface a GPR40 receptor, and containing a reporter construct comprising a responsive transcriptional element and a reporter gene, where expression of the reporter gene produces a detectable signal. The responsive transcriptional element may be a Gq responsive transcriptional element or a Gi/Gq responsive transcriptional element. The cell surface is exposed to (i.e., contacted with) a test compound and a GPR40 agonist, under conditions that permit binding of the GPR40 agonist to the GPR40 receptor. Subsequent reporter gene expression is detected, and decreased reporter gene expression in the presence of both test compound and agonist (compared to reporter gene expression expected in the presence of said GPR40 agonist only), indicates that the test compound is a GPR40 antagonist. As described previously herein, comparison of the reporter gene expression in the test cell may be made with a control cell, or to a known standard quantitative or qualitative response.

As used herein, a Gq responsive transcriptional element is one that responds (is activated) upon activation of a G$\alpha$q (or G$\alpha$q subtype) linked receptor. As is known in the art, Gq proteins are pertussis toxin insensitive G-proteins. As used herein, a Gi responsive transcriptional element is one that responds (is activated) upon activation of a G$\alpha$i (or G$\alpha$i subtype) linked receptor. As is known in the art, Gi proteins are pertussis toxin sensitive G-proteins (as are Go). As used herein, a Gq/Gi responsive transcriptional element is one that responds (is activated) upon activation of a G$\alpha$q-linked receptor (or G$\alpha$q subtypes), or a G$\alpha$I-linked receptor (or G$\alpha$I subtypes). One such Gq/Gi responsive transcriptional element is the GAL4/Elk-1 (see, e.g., Bevan et al., Neuroreport 9:2703 (1998)).

The present invention further provides methods of screening a compound for GPR40 antagonist activity, by detecting whether the compound decreases glucose-stimulated insulin release from mammalian pancreatic beta cells (or insulin production within mammalian pancreatic beta cells) in the presence of a GPR40 agonist, compared to glucose-stimulated insulin release that would occur due to the presence of the GPR40 agonist. the "expected" insulin release due to the presence of the GPR40 agonist may be established by carrying out a simultaneous or subsequent control experiment, or may have be a pre-determined standard. Various methods are known in the art for measuring insulin release from, or production within, cells. Any suitable method may be utilized in the present methods.

The present invention further provides a method of screening a compound for GPR40 agonist activity, by detecting whether the compound binds to GPR40 and increases glucose-stimulated insulin release from (or insulin production within) mammalian pancreatic beta cells.

Conversely, further receptors for which the fatty acid ligands of the invention act as ligands may be identified by screening potential candidates against a fatty acid ligand in a suitable assay, for instance determining potential inhibition of forskolin-elevated cAMP levels.

Kits suitable for carrying out the present methods may contain:

(a) GPR40 and one or more labeled or unlabeled fatty acid ligands;

(b) a recombinant cell expressing GPR40 and one or more labeled or unlabeled fatty acid ligands; or (c) a cell membrane expressing GPR40 and one or more labeled or unlabeled fatty acid ligands.

It will be appreciated that in any such kit, (a), (b), or (c) may comprise a substantial component.

Agonists and/or antagonists may be identified from a variety of sources, for instance, from cells, cell-free preparations, chemical libraries and natural product mixtures. Such agonists and/or antagonists may be natural or modified substrates, ligands, receptors, enzymes, etc., as the case may be, of any of the fatty acid ligands of the invention; or may be structural or functional mimetics of the polypeptide of the present invention (see Coligan et al, *Current Protocols in Immunology* 1(2):Chapter 5 (1991)).

Examples of potential antagonists include:

(a) antibodies or, in some cases, oligonucleotides, which bind to the receptor but do not elicit a second messenger response such that the activity of the receptor is prevented;

(b) fatty acids which are closely related to a ligand of GPR40 but which elicit no response from the GPR40 receptor;

(c) small molecules which bind to GPR40, making it inaccessible to ligands such that normal biological activity is prevented, for example, small peptides or peptide-like molecules;

(d) soluble forms of GPR40, e.g., fragments of the receptor, which bind to the ligand and prevent the ligand from interacting with membrane bound GPR40.

The invention further provides a method of rational drug design comprising the steps:

a) probing the structure of a fatty acid ligand-binding site on the GPR40 receptor with said fatty acid ligand or a derivative thereof;

b) identifying contacting atoms in the binding site of the GPR40 receptor that interact with a fatty acid ligand during binding; and c) designing agonist or antagonist compounds that interact with the atoms in the binding site identified in (b) to activate (agonist) or inhibit activation (antagonist) of the receptor.

Conversely, the structure of any of the fatty acids ligands when bound to the ligand binding site on the GPR40 receptor can also be determined, enabling the design of further antagonist compounds. Such antagonists bind to the fatty acid ligand, thereby preventing the binding of the fatty acid ligand to the receptor. Methods of using ligands or their derivatives to probe the structure of the ligand binding sites in receptors, and rational drug design based on this structural information are well known in the art (see for example Boyle, S et al *Bioorganic & Medicinal Chemistry* 1994, 2, 101–113; Beck-Sickinger, A. G et al, *European Journal Of Biochemistry* 1994, 225, 947–958; McWherter, C. A et al. *J. Biol. Chem.* 1997,1272, 11874–11880; Horwell, D. C et al.

*International Journal of Peptide & Protein Research* 1996, 48, 522–531; Bednarek, M. A. et al. *Peptides* 1999, 20, 401–409).

Compounds identified using the above screening or rational design methods will be of use in therapy. Accordingly, in a further aspect, the present invention provides a compound identified as an agonist or an antagonist of GPR40 for use in therapy, in particular for treating type II diabetes (non-insulin dependent daibetes mellitus, NIDDM) and obesity, glucose intolerance, insulin resistance, neurodegenerative disease (for example Alzheimer's disease) and other indications such as stroke, among others.

Accordingly, in a further aspect, this invention provides a method of treating an abnormal condition related to an excess of GPR40 activity and/or an excess of a GPR40 ligand (for example a fatty acid ligand). The method comprises administering to a patient in need thereof a GPR40 antagonist as hereinbefore described in an amount effective to block or decrease binding of ligands to the receptor, or to inhibit or decrease a second signal, thereby alleviating the abnormal condition.

In still another approach, expression of the gene encoding endogenous GPR40 polypeptide can be inhibited using expression blocking techniques. Known such techniques involve the use of antisense sequences, either internally generated or externally administered (see, for example, O'Connor, J Neurochem (1991) 56:560 in Oligodeoxynucleotides as Antisense Inhibitors of Gene Expression, CRC Press, Boca Raton, Fla. (19818)). Alternatively, oligonucleotides which form triple helices ("triplexes") with the gene can be supplied (see, for example, Lee et al., Nucleic Acids Res (1979) 6:3073; Cooney et al., Science (1988) 241:456; Dervan et al., Science (1991) 251:1360). These oligomers can be administered per se or the relevant oligomers can be expressed in vivo. Synthetic antisense or triplex oligonucleotides may comprise modified bases or modified backbones. Examples of the latter include methylphosphonate, phosphorothioate or peptide nucleic acid backbones. Such backbones are incorporated in the antisense or triplex oligonucleotide in order to provide protection from degradation by nucleases and are well known in the art. Antisense and triplex molecules synthesised with these or other modified backbones also form part of the present invention.

In addition, expression of the human GPR40 polypeptide may be prevented by using ribozymes specific to the human GPR40 mRNA sequence. Ribozymes are catalytically active RNAs that can be natural or synthetic (see for example Usman, N, et al., Curr. Opin. Struct. Biol (1996) 6(4), 527–33.) Synthetic ribozymes can be designed to specifically cleave GPR40 mRNAs at selected positions thereby preventing translation of the human GPR40 mRNAs into functional polypeptide. Ribozymes may be synthesised with a natural ribose phosphate backbone and natural bases, as normally found in RNA molecules. Alternatively the ribozymes may be synthesized with non-natural backbones to provide protection from ribonuclease degradation, for example, 2'-O-methyl RNA, and may contain modified bases.

Identification of a ligand for GPR40, such as a fatty acid ligand of the invention, allows for the effective identification of polyclonal or monoclonal antibodies raised against GPR40 which are neutralizing antibodies. Such neutralizing antibodies are of use in therapy, in comparison to non-neutralizing antibodies which are ineffective. Accordingly, in a further aspect, the present invention provides for the use of neutralizing antibodies raised against GPR40 in therapy.

Compounds which are active when given orally can be formulated as liquids, for example syrups, suspensions or emulsions, tablets, capsules and, lozenges. A liquid formulation will generally consist of a suspension or solution of the compound or pharmaceutically acceptable salt in a suitable liquid carrier(s) for example, ethanol, glycerine, non-aqueous solvent (for example polyethylene glycol), oils, or water with a suspending agent, preservative, flavouring or colouring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s) (for example aqueous gums, celluloses, silicates or oils) and the dispersion or suspension then filled into a soft gelatin capsule. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration. A typical suppository formulation comprises an active compound or a pharmaceutically acceptable salt thereof which is active when administered in this way, with a binding and/or lubricating agent such as polymeric glycols, gelatins or cocoa butter or other low melting vegetable or synthetic waxes or fats. The invention is further described in the following examples which are intended to illustrate the invention without limiting its scope. In order to facilitate understanding of the following examples certain methods and/or terms will be described.

All publications, including but not limited to patents and patent applications, cited in this specification are herein incorporated by reference as if each individual publication were specifically and individually indicated to be incorporated by reference herein as though fully set forth.

EXAMPLES

Example 1

TAQMAN® Analysis of GPR40 Expression in Human Tissues

Generation of samples for TAQMAN® mRNA analysis:

TAQMAN® PCR was performed following the procedure published by Sarau H. M. et al, ("Identification, Molecular Cloning, Expression and Characterisation of a Cysteinyl Leukotriene Receptor", Molecular Pharmacology, 1999, 56, 657–663.) TAQMAN® quantitative PCR was conducted to measure GPR40 mRNA using replicate 96-well plates. A 20 µl volume of a PCR master mix (containing 2.5 µl TAQMAN® buffer, 6 µl 25 mM $MgCl_2$, 0.5 µl of 10 mM dATP, 0.5 µl of 20 mM dUTP, 0.5 µl of 10 mM dCTP, 0.5 µl of 10 mM dGTP, 0.25 µl Uracil-N-glycosylase, 1 µl of 10 µM forward primer, 1 µl of 10 µM reverse primer, 0.5 µl 5 µM TAQMAN® probe, 0.125 µl TaqGold [PE Biosystems], 6.625 µl water) was added to each well using Biomek robotics (Beckman Coulter, High Wycombe, UK), and the plate capped using optical caps (PE Biosystems). The PCR reaction was carried out on an ABI7700 Sequence Detector (PE Biosystems) using the PCR parameters: 50° C. for 2 minutes, 95° C. for 10 minutes and 45 cycles of 94° C. for 15 seconds, 60° C. for 1 minute, and the level of mRNA-derived cDNA in each sample was calculated from the TAQMAN® signal using plasmid/genomic DNA calibration standards included in each run. The level of genomic DNA contaminating the original RNA samples was shown to be negligible (<10 copies genomic DNA/ng RNA) by TAQ-MAN® measurement of genomic sequence for ten genes in replicate samples taken through the reverse transcription procedure described with the omission of reverse transcriptase. Gene-specific reagents for GPR40:

```
                                             (SEQ ID NO: 5)
forward primer:    5' GTGGTGCTTAATCCGCTGGT (SEQ ID NO: 6)
reverse primer:    5' TGGCGTTACTTCTGGGACTTG (SEQ ID NO: 7)
probe:             5' CTTGCGTTCTTGCCGCACACACTGT
```

The results show that the highest levels of GPR40 are expressed in the pancreas; results are shown in Table 1

TABLE 1

GPR40 Body tissue mRNA levels
units: copies of GPR40 mRNA detected/ng mRNA pool

|  | mean mRNA copies | +/−SEM |
|---|---|---|
| Brain | 111 | 12 |
| Pituitary | 46 | 18 |
| Heart | 91 | 47 |
| Lung | 30 | 15 |
| Liver | 28 | 11 |
| Foetal Liver | 59 | 28 |
| Kidney | 24 | 13 |
| Muscle | 44 | 10 |
| Stomach | 22 | 7 |
| intestine | 34 | 21 |
| Spleen | 61 | 4 |
| Lymphocytes | 62 | 24 |
| Macrophage | 7 | 7 |
| adipose | 30 | 6 |
| Pancreas | 225 | 44 |
| Prostate | 78 | 32 |
| Placenta | 31 | 11 |
| Cartilage | 5 | 6 |
| Bone | 30 | 11 |
| Bone marrow | 20 | 12 |

Example 2

Expression of GPR40 in Human Pancreatic Islet Cells

TAQMAN® analysis of human pancreatic islet RNA vs total pancreatic RNA was carried out as described in Example 1. For an equivalent RNA sample from islet cells and total pancreas, in 3 independent islet samples there was a 2 to 100 fold higher expression of GPR40 than in total pancreas. (Results not shown).

Example 3

Expression of GPR40 in MIN6 and BRIN Insulinoma Cells

TAQMAN® Conditions for Mouse and Rat GPR40 Expression:

TAQMAN® was performed using 50 ng cDNA per reaction with 0.3 µM forward primer, 0.3 µM reverse Primer, 0.1 µM probe and 1× TAQMAN® Master Mix (PE Applied Biosystems, UK). The cycle conditions were as follows 50° C. for 2 min, 95° C. for 10 min followed by 40 cycles of 95° C. for 15 secs, 60° C. for 1 min.

Primer/Probe Sets for Mouse/Rat GPR40

```
                                             (SEQ ID NO: 8)
Forward Primer:    5' AGTTCCCTGGGCATCAACATA3'

(SEQ ID NO: 9)
Reverse Primer:    5' CAAGGGCAGAAAGAAGAGCAGA3'

(SEQ ID NO: 10)
Probe:             5' AATGGCTCCCCGGTCTGCCTGG3'
```

Results are shown in Table 2. Results show that GPR40 was expressed in both insulinoma cell-lines, confirming β-cell localisation. The results further showed that expression of GPR40 in MIN6 cells is much greater than in BRIN cells.

TABLE 2

| Insulinoma cell line | Av Ct value[1] | Relative value (mouse std curve) normalised (HPRT[2]) | Relative value (rat std curve) normalised (HPRT[2]) |
|---|---|---|---|
| MIN6 (Mouse Insulinoma) | 22.7 | 0.95 | 119946.9 |
| BRIN (rat insulinoma) | 37.1 | $3.23 \times 10^{-5}$ | 0.09 |

[1]Ct value refers to the cycle number of TAQMAN ® necessary to detect gene expression for that transcript.
[2]HPRT = Hypoxanthine-Guanine Phosphoribosyltransferase Example 4

GPR40 Expression is Increased in ob/ob Mouse Pancreas

TAQMAN® analysis was carried out to determine GPR40 levels in C57B1/6 lean mice compared with C57B 1/6 ob/ob homozygous knock-out mice. These levels were further compared with levels of insulin mRNA. The results are shown in Table 3.

TABLE 3

| | Relative Quantity GPR40[1] (mRNA ± s.e.m.) | Relative Quantity Insulin[1] (mRNA ± s.e.m.) |
|---|---|---|
| C57/B1/6 lean mice (n = 10) | 12 ± 28 | 78 ± 7 |
| C57B1/6 ob/ob mice (n = 10) | 113 ± 23 | 960 ± 145 |

[1]relative measure from a standard curve created using known amounts of cDNA made from total RNA with random primers.

Example 5

GPR40 and Fatty Acids—Receptor Ligand Pairing

Cells expressing the GPR40 receptor exhibit a dose-related increase in intracellular calcium levels in response to fatty acid ligands, as measured by FLIPR technology. FIG. 1 shows the FLIPR response detected following addition of elaidic acid (trans oleic acid, 9-octadecanoic acid) to HEK-293 cells transiently expressing the GPR40 receptor. No response was detected in cells transiently expressing two other 7TM receptors (PGRW and HLTEX11). The assays utilized a G-protein cocktail (+GPC) that contained chimeric and promiscuous G-proteins, as is known in the art of screening orphan G-protein coupled receptors.

GPR40 stimulation by other fatty acid ligands, using FLIPR technology as described herein, is shown in Table 4 below (pEC50=–log EC50 where EC50 is 'effective concentration'; EC50 is half of the concentration of compound necessary for a maximal response)

TABLE 4

| | Mean pEC50 | Mean pEC50 | Mean pEC50 | | Mean pEC50 of 3 expts | (+/−) sem |
|---|---|---|---|---|---|---|
| Unsaturated Fatty Acids | | | | | | |
| Palmitoleic acid $C_{16}H_{30}O_2$ (9Z) | 4.82 | 4.81 | 4.96 | | 4.86 | 0.05 |
| Linolenic acid $C_{18}H_{30}O_2$ (9Z, 12Z, 15Z) | 4.93 | 4.66 | 5.12 | | 4.90 | 0.13 |
| Linoleic acid $C_{18}H_{32}O_2$ (9Z, 12Z) | 4.78 | 4.68 | | | 4.73 | n = 2 |
| 12. Elaidic acid $C_{18}H_{34}O_2$ (9E) | 5.03 | 5.27 | 5.18 | | 5.16 | 0.07 |
| Oleic acid $C_{18}H_{34}O_2$ (9Z) | 4.55 | 4.23 | | | 4.39 | n = 2 |
| Petroselinic acid $C_{18}H_{34}O_2$ (6Z) | 4.88* | 4.97 | 5.03 | | 5.00 | 0.02 |
| All-trans-retinal (Vitamin A aldehyde) $C_{20}H_{28}O$ | 4.08 | 4.23 | | | 4.16 | n = 2 |
| All-trans-retinoic acid (Vitamin A acid; Tretinoin) $C_{20}H_{28}O_2$ | 5.56 | 5.52 | 5.65 | | 5.58 | 0.04 |
| 9-cis-retinoic acid (9-cis-tretinoin) $C_{20}H_{28}O_2$ | 4.27 | 4.52 | | | 4.40 | n = 2 |
| All-trans-retinol (Vitamin A) $C_{20}H_{30}O$ | No Fit | No Fit | | | | |
| Arachidonic acid $C_{20}H_{32}O_2$ (5Z, 8Z, 11Z, 14Z) | 4.74 | 4.89 | 5.14 | | 4.92 | 0.12 |
| cis-4,7,10,13,16,19-Docosahexaenoic acid $C_{22}H_{32}O_2$ | 5.18 | 5.53 | 5.4 | | 5.37 | 0.10 |
| Erucic acid $C_{22}H_{42}O_2$ (13Z) | 4.33* | No Fit | | | 4.33 | n = 1 |
| Nervonic acid $C_{24}H_{46}O_2$ (15Z) | No Fit | No Fit | | | | |
| Saturated Fatty Acids | | | | | | |
| n-caproic acid $C_6H_{12}O_2$ | 4.33* | No Fit | | 6 | 4.33 | n = 1 |
| Heptanoic acid $C_7H_{14}O_2$ | 4.33 | 4.22* | | 7 | 4.28 | n = 2 |
| Caprylic acid $C_8H_{16}O_2$ | 4.25 | 4.58 | | 8 | 4.42 | n = 2 |
| Nonanoic acid $C_9H_{18}O_2$ | 4.16 | 4.63 | | 9 | 4.40 | n = 2 |
| Capric acid $C_{10}H_{20}O_2$ | 4.74 | 4.96 | 4.84 | 10 | 4.85 | 0.06 |
| Undecanoic acid $C_{11}H_{22}O_2$ | 4.6 | 4.66 | 4.83 | 11 | 4.70 | 0.07 |
| Lauric acid (Dodecanoic acid) $C_{12}H_{24}O_2$ | 4.75 | 4.93 | 5.07 | 12 | 4.92 | 0.09 |
| Tridecanoic acid $C_{13}H_{26}O_2$ | 4.8 | 4.95 | 5.05 | 13 | 4.93 | 0.07 |
| Myristic acid $C_{14}H_{28}O_2$ | 4.95 | 4.52 | 5.05 | 14 | 4.84 | 0.16 |
| Pentadeconoic acid $C_{15}H_{30}O_2$ | 4.97 | 5.36 | 5.21 | 15 | 5.18 | 0.11 |
| Palmitic acid $C_{16}H_{32}O_2$ | 5.08 | 5.51 | 5.3 | 16 | 5.30 | 0.12 |
| Heptadecanoic acid $C_{17}H_{34}O_2$ | 4.86 | 4.99 | 5.11 | 17 | 4.99 | 0.07 |
| Stearic acid $C_{18}H_{36}O_2$ | 4.7 | 4.78 | 4.85 | 18 | 4.78 | 0.04 |
| Nonadecanoic acid $C_{19}H_{38}O_2$ | 4.58 | 4.46* | | 19 | 4.52 | n = 2 |
| Arachidic acid $C_{20}H_{40}O_2$ | No Fit | 4.21* | | 20 | 4.21 | n = 1 |
| Heneicosanoic acid $C_{21}H_{42}O_2$ | 4.45 | 4.53* | | 21 | 4.49 | n = 2 |
| Behenic acid (Docosanoic acid) $C_{22}H_{44}O_2$ | 4.29 | 4.31 | | 22 | 4.30 | n = 2 |

TABLE 4-continued

| | | | | | |
|---|---|---|---|---|---|
| Tricosanoic acid $C_{23} H_{46} O_2$ | 4.31* | No Fit | 23 | 4.31 | n = 1 |
| Lignoceric acid $C_{24} H_{48} O_2$ | No Fit | No Fit | 24 | 0 | |

| Additional Fatty Acid Compounds | EC50 (M) | EC50 uM | pEC50 |
|---|---|---|---|
| Mean acid (10:3, n-9) | 2.51E−06 | 2.5 | 5.60 |
| Linoleic acid (18:2, n-6) | 9.54E−06 | 9.5 | 5.02 |
| Linolenic acid (18:3, n-3) | 5.50E−06 | 5.5 | 5.26 |
| Gamma-Linolenic acid (18:3, n-6) | 8.91E−06 | 8.9 | 5.05 |
| Elaidic acid (18:1, n-9, E) | 1.35E−05 | 13.5 | 4.87 |
| 17-Octadecynoic acid (17-ODYA) (18:1 x terminal acetylene | 7.58E−06 | 7.6 | 5.12 |
| Eicosa-11Z,14Z-dienoic acid (20:2, n-6) | 1.07E−05 | 10.7 | 4.97 |
| Eicosa-5Z,8Z-dienoic acid (20:2, n-12) | 7.76E−06 | 7.8 | 5.11 |
| Eicosa-11Z,14Z,17Z-trienoic acid (20:3, n-3) | 1.12E−05 | 11.2 | 4.95 |
| Dihomo-gamma-linolenic acid (20:3, n-6) | 7.24E−06 | 7.2 | 5.14 |
| 5,8,11-Eicosatriynoic acid (20:3 x acetylenes) | 1.70E−06 | 1.7 | 5.77 |
| Eicosa-5Z,8Z,11Z,14Z,17Z-pentaenoic acid (20:5, n-3) | 6.76E−06 | 6.8 | 5.17 |
| Arachidonic acid (20:4, n-6) | 9.12E−06 | 9.1 | 5.04 |
| 14 ®, 15(S)-DiHETE (20:4 + 2 hydroxyls) | 2.34E−05 | 23.4 | 4.63 |
| Docosa-13Z,16Z,19Z-trienoic acid (22:3, n-3) | 6.76E−06 | 6.8 | 5.17 |
| Adrenic acid (22:4, n-6) | 1.35E−05 | 13.5 | 4.87 |
| Docosa-7Z,10Z,13Z,16Z,19Z-pentaenoic acid (22.5, n-3) | 4.68E−06 | 4.7 | 5.33 |
| Docosa-4Z,7Z,10Z,13Z,16Z,19Z-hexaenoic acid (22:6, n-3) | 1.62E−06 | 1.6 | 5.79 |

Example 5A

Functional Assays

G-Protein Coupling

Most GPCRs show constitutive activity as expression of the GPCR increases. Experiments were performed to determine whether GPR40 couples through $G\alpha_s$, $G\alpha_q$ or $G\alpha_i$, using constitutively active reporters and following agonist activation.

Constitutive GPR40 activity was examined in melanophores. The melanophores were transiently transfected with 10, 20, 40 and 80 ug of GPR40/pJG3.6 plasmid DNA by electroporation and plated into 96-well plates. Forty-eight hours post-electroporation, media was aspirated and replaced with L-15 assay buffer, assay buffer+25 nM Melatonin or assay buffer+100 nM alpha-MSH. These reagents were allowed to incubate for 2 hours and the transmittance (T) was read. Percent constitutive activity was calculated using the following calculation:

$$\frac{(T(L15) - T(MSH))}{(T(\text{Melatonin}) - T(MSH))} * 100$$

Figure 2:
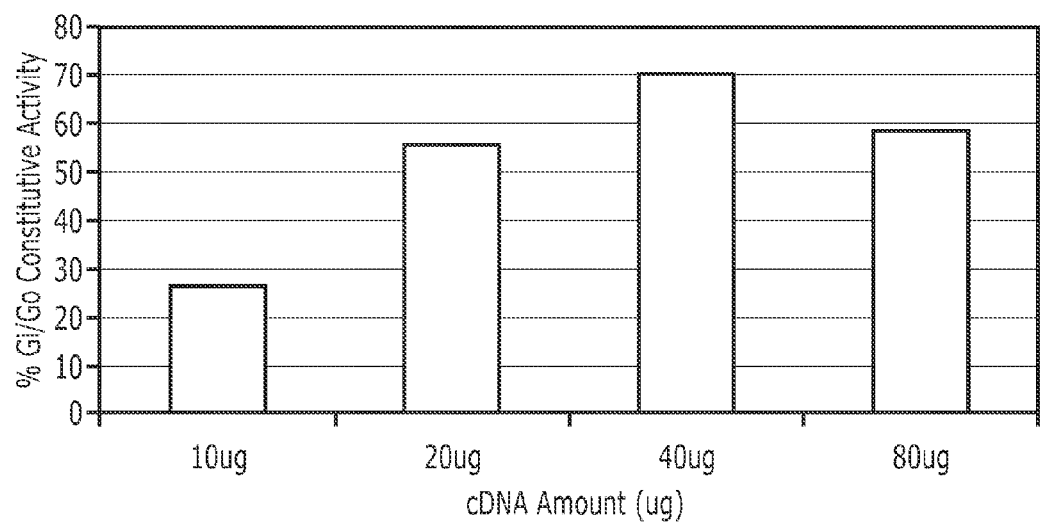
FIG. 2 shows the results of assays using transiently transfected melanophores to determine the G-protein coupling of GPR40. Increasing amounts of transfected GPR40 DNA produced an increase in $G\alpha_i/G\alpha_o$ activity, indicating that constitutive activity of GPR40 is through $G\alpha_i$.

Results show that increasing amounts of transfected GPR40 DNA produced an increase in the $G\alpha_i/G\alpha_o$ activity, indicating that constitutive activity of GPR40 is through either the $G\alpha_i/G\alpha_o$ family of G-proteins. (FIG. 2)

Specific coupling was determined in mammalian cells using transient expression of a CRE-luciferase reporter for $G\alpha_s$ and stable cell-lines containing Gal4/ELK-1-luciferase reporter for $G\alpha_q/G\alpha_i$. Wild-type CHO cells were co-transfected with 3×-CRE-luciferase reporter vector and various amounts of an expression vector for GPR40. The control cells were transfected with reporter vector only. The reporter gene plasmids were produced in house but similar vectors can be purchased from Stratagene (PATHDETECT®). Cells were plated in a 24 well tissue culture plate at 1×10⁴ cells/well in DMEM/F12 supplemented with 5% FBS. After 72 hours at 37° C., 5% $CO_2$, the cells were transfected using the liposomal transfection reagent sold under the trademark LIPOFECTAME® and with the following combinations of plasmids:

A-3×-CRE-Luc
B-3×-CRE-Luc+CMV-GPR40
C-3×-CRE-Luc+CMV-Gs coupled receptor

The concentration of reporter plasmid for all wells was 0.15 µg/well. Concentrations of receptor plasmids were 0.5, 1.0, 5.0, 10.0 ng/well. After 24 hrs Cells containing 1 ng/well of receptor plasmid or no DNA control and CRE-Luc reporter were treated with fatty acid or the calcitonin which is known to act through a Gs-coupled receptor (Chakraborty, Science 251: 1078 (1991)) at concentrations indicated. Luciferase production was assayed after 4 hours of treatment using a luciferase reporter gene assay kit available under the trademark LUCLITE®, used per manufacturers instructions (Packard Bioscience).

Figure 3A:
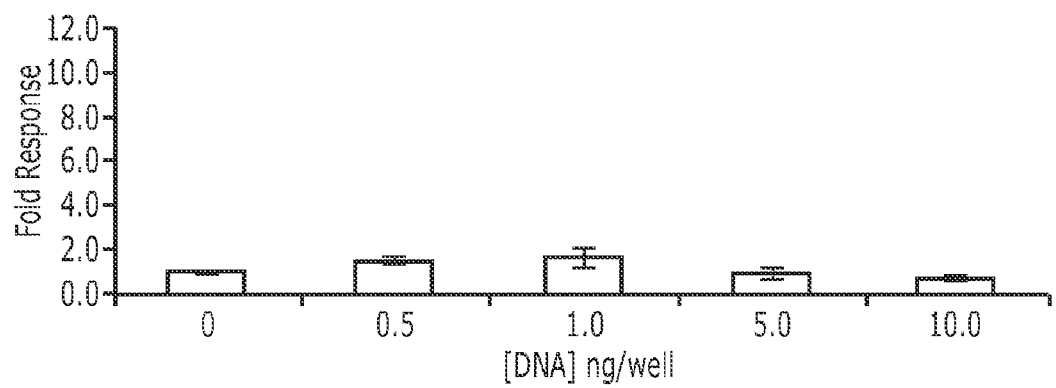
FIG. 3a graphs the fold-response of CHO cells expressing CRE-luciferase human GPR40; there was no increase in reporter activity detected in the CRE system at any dose of GPR40 expression vector.
Figure 3B:
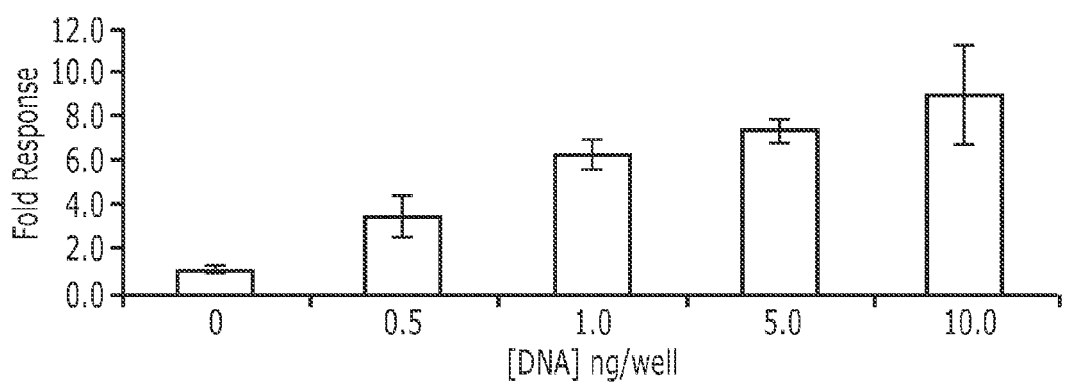
FIG. 3b graphs the fold-response of CHO cells expressing CRE-luciferase Human Gs-coupled receptor; there was significant increase in luciferase activity detected with increasing doses of expression vector.

As shown in FIG. 3a, there was no increase in reporter activity in the CRE system at any dose of GPR40 expression vector. In contrast, as shown in FIG. 3b, expression of a Gs-coupled receptor elicited a significant increase in luciferase activity.

Figure 3C:
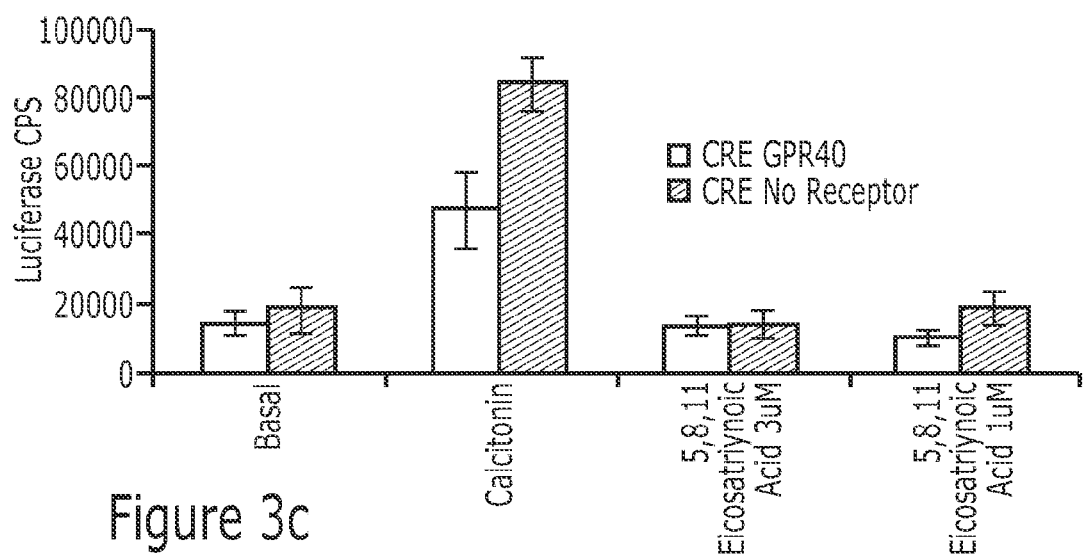
FIG. 3c graphs the effect of calcitonin and eicosatriynoic acid on luciferase activity from CHO cells expressing CRE-luciferase human GPR40 or CHO cells expressing CRE-luciferase with no receptor. Luciferase production was increased by calcitonin in both the cells containing reporter only and cells containing GPR40, whereas no significant effect of 5,8,11 Eicosatriynoic acid was detected at any concentration tested.

As shown in FIG. 3c, although calcitonin elicited an increase in luciferase production in both the cells containing reporter only and those containing GPR40, there was no effect of 5,8,11 Eicosatriynoic acid at any concentration tested, indicating that neither GPR40 constitutive nor agonist-activated activity is coupled via Gαs.

To further test the coupling of GPR40 to $G\alpha_i/G\alpha_q$ a Gal4/Elk-1 reporter was used. A stable, clonal reporter line was created by transfecting CHO cells with a plasmid that contains an expression construct for GAL4/Elk-1 and a GAL4-luciferase reporter construct. A similar reporter system can now be purchased from Stratagene (under the trademark PATHDETECT®). An expression construct for human GPR40 which contains a G418 resistance construct was transfected into the host CHO GAL4/Elk-1 reporter cell line (10 ug plasmid DNA pCR3-GPR40) via electroporation. The cell lines were selected for with 500 ug/mL G418 until all cells in the control were dead and clones were then picked. The Gal4/Elk-1 reporter can be activated through Gq or Gi. To confirm coupling via Gi, cells were treated with pertussis toxin treatment which ADP-ribosylates Gαi preventing its interaction with receptors (Bokoch et al., J. Biol. Chem 258:2072 (1983)). Pertussis toxin has no known effect on Gαq.

Host cells and those transfected with the GPR40 construct were plated in a 96-well tissue culture plate at 2000 cells/well in DMEM/F12 supplemented with 5% FBS. After 48 hours at 37° C. at 5% $CO_2$, the cells were placed in serum-free DMEM/F12 in the presence or absence of 1 ug/ml pertussis toxin. After 16 hours at 37° C., 5% $CO_2$ the host cells were treated with: lysophosphatidic acid (oleoyl) (LPA) which couples through $G\alpha_i$ to activate MAP kinase (Hordijk et al., J. Biol. Chem. 269: 645 (1994)); thrombin which couples through Gαi and Gαq (Hung et al., J. Biol. Chem. 267:20831 (1992)); or 5,8,11-Eicosatriynoic acid (a GPR40 ligand), at the concentrations indicated. The host cells containing the GPR40 construct were stimulated with or 5,8,11-Eicosatriynoic acid at the concentrations indicated. Controls for lysophosphatidic acid contained 0.5% DMSO; controls for 5,8,11-eicosatrienoic acid contained 0.05% ethanol. Luciferase activity was assayed 4 hours after treatment using a luciferase reporter gene assay kit available under the trademark LUCLITE®, as per manufacturers instructions (Packard Bioscience).

Figure 4A:
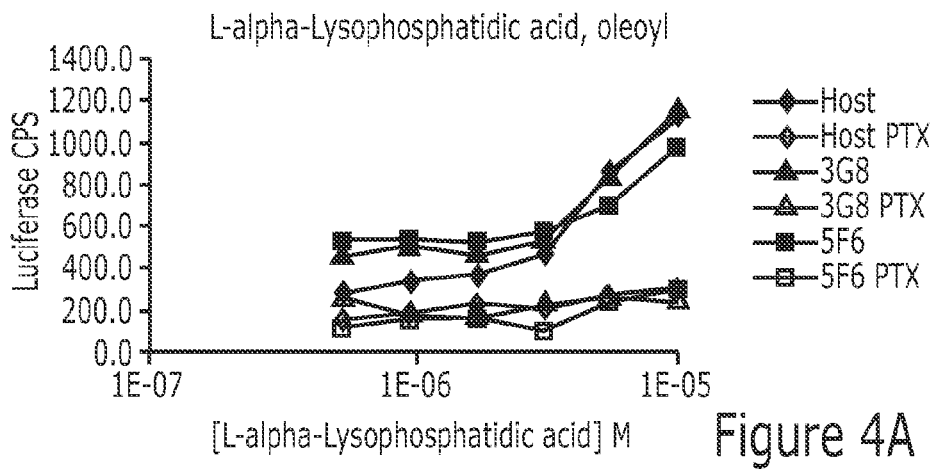
FIG. 4A shows changes in L-alpha-Lysophosphatidic acid (LPA) stimulated reporter activity, with and without pertussis toxin (PTX) treatment. Host cells consisted of CHO cells containing GAL4/Elk1-luciferase reporter constructs; 3G8 and 5F6 are clonal CHO cell lines transfected with human GPR40 and containing GAL4/Elk1-luciferase reporter construct. Luciferase production in host cells due to LPA-stimulation was abolished by pertussus toxin treatment.
Figure 4B:
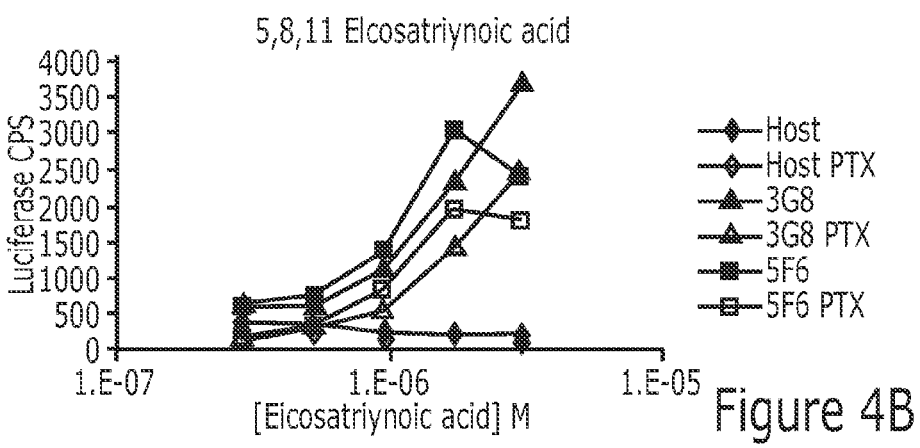
FIG. 4B shows changes in 5,8,11-Eicosatriynoic acid stimulated reporter activity, with and without pertussis toxin (PTX) treatment. Cells are as described for FIG. 4A. Luciferase production due to 5,8,11-Eicosatriynoic acid stimulation was increased in cells transfected with GPR40, and was not inhibited by pertussis toxin treatment.

As shown in FIG. 4A, in the host cells LPA-stimulated reporter activity was completely abolished by the pertussis toxin treatment confirming coupling through $G\alpha_i$.

Figure 4C:
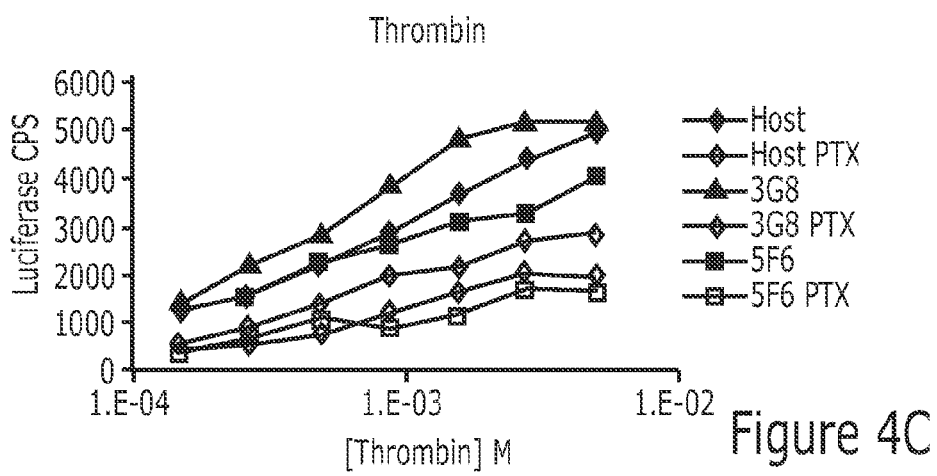
FIG. 4C shows changes in thrombin stimulated reporter activity, with and without pertussis toxin (PTX) treatment. Cells are as described for FIG. 4A. Luciferase production due to thrombin stimulation was only partially attenuated following pertussis toxin treatment.

As shown in FIG. 4C, luciferase production due to thrombin stimulation was only partially attenuated following toxin treatment confirming Gαi/Gαq coupling.

Figure 4D:
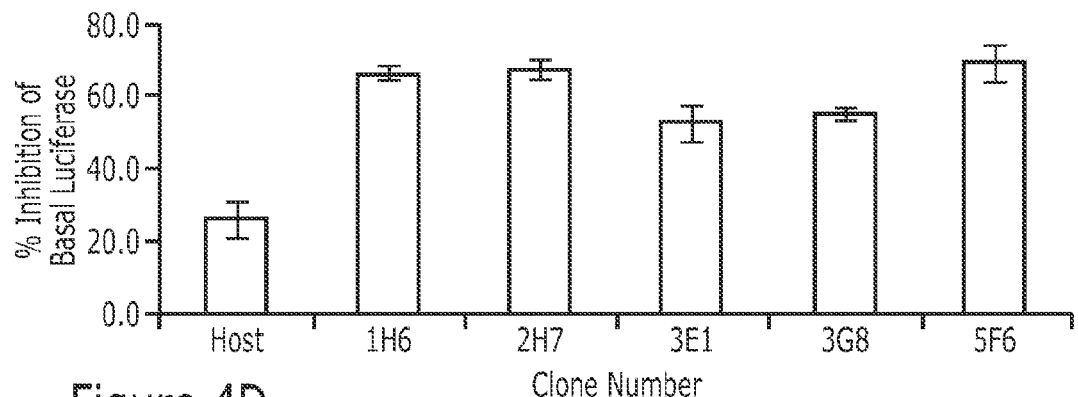
FIG. 4D shows the percent inhibition of luciferase activity following pertussin toxin treatment in CHO cells expressing GAL4/ELK1-luciferase only (host cell), and five different CHO cell clones expressing GAL4/ELK1-luciferase and human GPR40.
Figure 4E:
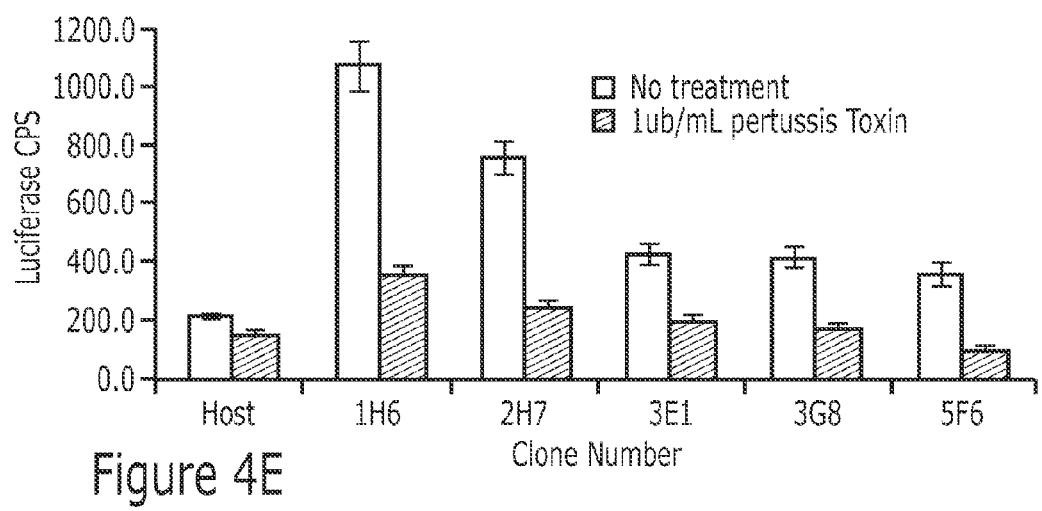
FIG. 4E shows basal luciferase counts from CHO cells expressing GAL4/Elk1-luciferase only (host cell), and different CHO cell clones expressing GAL4/ELK1-luciferase and human GPR40, either with or without pertussis toxin treatment. Clones transfected with GPR40 expression construct and ELK-Gal4 reporter exhibited an increased basal reporter activity compared to that of the host cell line, but this was decreased by up to 70% following pertussis toxin treatment.

As shown in FIGS. 4D and 4E, clones transfected with GPR40 expression construct and ELK-Gal4 reporter exhibited an increase in basal reporter activity versus the host cell line containing reporter alone, which was decreased by up to 70% following pertussis toxin treatment suggesting constitutive $G\alpha_i$ coupled receptor activity.

As shown in FIG. 4B, 5,8,11-Eicosatriynoic acid had no effect on luciferase production in the host cells, but increased luciferase activity compared to basal in cells containing GPR40 in a manner which was not inhibited by pertussis toxin treatment.

These assays demonstrate that constitutive GPR40 receptor activity is coupled to the $G\alpha_I$ or $G\alpha_o$ (and related family members) pertussis toxin sensitive G-rproteins. Furthermore, fatty acid agonist stimulated GPR40 receptor activation is coupled through a pertussis-toxin insensitive G-protein, suggesting that agonist-stimulated GPR40 receptor activation is coupled through Gαq.

Example 6

Functional Assays

Calcium Assay

Receptors stably expressed in HEK 293 cells can demonstrate a robust calcium response to agonists with the appropriate rank order and potency. Basal calcium levels in the HEK 293 cells in GPR40-transfected or vector control cells are in the normal 100 nM to 200 nM range. HEK 293 cells expressing recombinant GPR40 receptors are loaded with the fluorescent indicator FLUO-4 and in a single day>150 selected ligands are evaluated for agonist-induced calcium mobilization. Agonists presenting a transient calcium mobilization are tested in vector control cells to determine if the calcium response is unique to the transfected receptor cells. When a unique agonist-induced response is identified, the response is reproduced in a separate group of cells and then pharmacologically characterized with concentration response curves for the effective and related ligands.

Example 7

Membrane Preparation and Screen for GPR40

Fatty acid ligand binding competition assays are useful for the discovery of antagonists and agonists of the GPR40 receptor. As a source of the GPR40 receptor, CHO or HEK 293 cells stably transfected with the GPR40 receptor are useful; other cells transfected with the GPR40 receptor or cells that naturally show a high level expression of the GPR40 receptor may also be employed. Typically the culture of cells expressing the GPR40 receptor is scaled up to 30 L and cells are recovered by centrifugation at 600×g for 10 min. The cell pellet is then frozen in liquid nitrogen. Pellets usually contain around $10^9$ cells. For membrane isolation, pellets are freeze/thawed 3 times. They are then resuspended in ice cold 10 mM Tris (pH 7.5), 1 mM EDTA (sodium salt) (40 mls/1e8 cells) and homogenized using a Dounce (glass/glass) homogenizer (20–25 strokes), followed by a Polytron suspension with 3–10 sec pulses on a ¾ setting (Brinkman tissue homogenizer). This suspension is centrifuged at 300×g for 10 min. The pellet is discarded and the supernatent fraction is centrifuged at 40,000×g (Sorvall SS-34: 18,000 rpm) for 30 min. at 4° C., resuspended in homogenizing buffer using the polytron, and washed one time. The pellet is resuspended in assay buffer (50 mM Tris pH 7.5) at a concentration of 1–4 mg protein/ml.

Membranes obtained this way are suitable for the set-up of a high throughput fatty acid ligand binding competition assay to search for compounds that interfere in the ligand-receptor interaction. The total binding of a labelled fatty acid to these membranes is first tested to be linear with the amount of membranes used. The time period to reach equilibrium binding at a suitable temperature is also established and is in our experience about 1 h at a temperature of 20° C. Conditions for such a screening assay are exemplified by those used in MCH receptor binding. Typically 25 μg of membrane protein per well is used in a total volume of 100 μl buffer containing 50 mM HEPES, 1 mM CaCl$_2$, 5 mM MgCl$_2$ and 0.5% Bovine serum albumin (western blot quality), pH 7.4. The concentration of $^{125}$I-mMCH is typically 1–2 nM and 75,000 cpm/well. Specific binding of $^{125}$I-mMCH should be displaced completely by unlabeled MCH at concentrations of 100 nM or more.

The compounds to be tested are typically dissolved and added in DMSO and final concentrations of DMSO in the assay are 1% or less. After incubation the contents of the wells are harvested on a polyethyleneimine-treated GF/C filter using a 96 well plate cell harvester and the filters are washed four times with typically 1 ml icecold wash buffer containing 20 mM HEPES 0.5M NaCl pH 7.4. The filters are counted to identify antagonists of labelled fatty acid ligand binding.

That which is claimed is:

1. A method of screening a test compound to determine whether the test compound is a GPR40 receptor ligand, comprising detecting whether said test compound competitively inhibits the binding of a fatty acid GPR40 receptor ligand to said GPR40 receptor, wherein said GPR40 receptor comprises the amino acid sequence of SEQ ID NO: 2, and wherein said fatty acid GPR40 receptor ligand is a C6–C23 saturated or unsaturated fatty acid, optionally containing up to 6 alkene or 3 acetylene bonds, optionally cyclic or branched, and optionally substituted with 1–3 hydroxy groups.

2. The method according to claim 1, wherein said fatty acid GPR40 receptor ligand is labeled with a detectable label.

3. The method according to claim 1, wherein said GPR40 receptor is provided by cell membranes.

* * * * *